United States Patent
Ushio et al.

(10) Patent No.: US 8,445,263 B2
(45) Date of Patent: May 21, 2013

(54) DEVICE FOR CELLULAR ELECTROPHYSIOLOGY SENSOR, CELLULAR ELECTROPHYSIOLOGY SENSOR USING THE DEVICE, AND METHOD FOR MANUFACTURING THE CELLULAR ELECTROPHYSIOLOGY SENSOR DEVICE

(75) Inventors: Hiroshi Ushio, Hyogo (JP); Masaya Nakatani, Hyogo (JP); Soichiro Hiraoka, Osaka (JP); Akiyoshi Oshima, Osaka (JP); Makoto Takahashi, Osaka (JP)

(73) Assignee: Panasonic Corporation, Osaka (JP)

( * ) Notice: Subject to any disclaimer, the term of this patent is extended or adjusted under 35 U.S.C. 154(b) by 201 days.

(21) Appl. No.: 12/301,307

(22) PCT Filed: Jun. 27, 2007

(86) PCT No.: PCT/JP2007/062887
§ 371 (c)(1),
(2), (4) Date: Nov. 18, 2008

(87) PCT Pub. No.: WO2008/004476
PCT Pub. Date: Jan. 10, 2008

(65) Prior Publication Data
US 2009/0281410 A1   Nov. 12, 2009

(30) Foreign Application Priority Data

Jul. 6, 2006 (JP) ................. 2006-186411
Jul. 6, 2006 (JP) ................. 2006-186412
Aug. 8, 2006 (JP) ................. 2006-215303
Aug. 8, 2006 (JP) ................. 2006-215304

(51) Int. Cl.
*C12M 1/34* (2006.01)

(52) U.S. Cl.
USPC ..................... 435/287.1; 204/403.1

(58) Field of Classification Search
USPC ..................... 435/287.1; 204/403.1
See application file for complete search history.

(56) References Cited

U.S. PATENT DOCUMENTS 5,183,744 A    2/1993  Kawamura et al.
5,711,702 A *  1/1998  Devlin ................. 451/540
(Continued)

FOREIGN PATENT DOCUMENTS

EP   0 652 308 B1   3/2002
EP   1 533 615 A2   5/2005
(Continued)

OTHER PUBLICATIONS

Wild et al., "Locally selective bonding of silicon and glass with laser", 2001, Sensors and Actuators, A 93, pp. 63-69.*

(Continued)

*Primary Examiner* — Michael Marcheschi
*Assistant Examiner* — Jonathan Hurst
(74) *Attorney, Agent, or Firm* — RatnerPrestia (57) ABSTRACT

A leakage current on a side surface of a sensor chip of a cell electrophysiological sensor is reduced. In order to do so, a sensor chip having a continuity hole and a chip holding part covering the side surface of the sensor chip are provided. The sensor chip includes silicon as a main component, and the chip holding part is made of glass. The chip holding part is adhesively bonded to the side surface of the sensor chip by glass welding. Thus, in the cell electrophysiological sensor device of the present invention, the airtightness between the side surface of the sensor chip and the chip holding part is improved, so that a leakage current can be reduced.

16 Claims, 8 Drawing Sheets

U.S. PATENT DOCUMENTS

| | | |
|---|---|---|
| 6,682,649 B1 | 1/2004 | Hansen et al. |
| 6,776,896 B1 | 8/2004 | Osipchuk |
| 6,932,893 B2 | 8/2005 | Bech et al. |
| 6,984,297 B2 | 1/2006 | Nisch et al. |
| 7,006,929 B2 | 2/2006 | Oka et al. |
| 7,494,622 B2 | 2/2009 | Picollet-Dahan et al. |
| 7,501,278 B2 | 3/2009 | Nakatani et al. |
| 2001/0046706 A1 | 11/2001 | Rubinsky |
| 2002/0074227 A1 | 6/2002 | Nisch |
| 2003/0107386 A1 | 6/2003 | Dodgson |
| 2003/0113833 A1 | 6/2003 | Oka et al. |
| 2004/0033483 A1 | 2/2004 | Oka et al. |
| 2005/0058990 A1 | 3/2005 | Guia et al. |
| 2005/0112756 A1 | 5/2005 | Nakatani et al. |
| 2005/0214740 A1 | 9/2005 | Ushio et al. |
| 2005/0221469 A1 | 10/2005 | Nakatani et al. |
| 2006/0163063 A1 | 7/2006 | Picollet-Dahan |
| 2007/0105183 A1 | 5/2007 | Nakatani et al. |
| 2009/0178922 A1 | 7/2009 | Nakatani et al. |
| 2009/0239033 A1 | 9/2009 | Nakatani et al. |

FOREIGN PATENT DOCUMENTS

| | | | |
|---|---|---|---|
| FR | 2844052 A1 | 3/2004 | |
| JP | 02-131569 A | 5/1990 | |
| JP | 06-244257 A | 9/1994 | |
| JP | 2002-518678 A | 6/2002 | |
| JP | 2003-511668 A | 3/2003 | |
| JP | 2003-511699 A | 3/2003 | |
| JP | 2003-527581 | 9/2003 | |
| JP | 2004-12215 A | 1/2004 | |
| JP | 2004-045358 A | 2/2004 | |
| JP | 2004-510980 A | 4/2004 | |
| JP | 2004-166692 A | 6/2004 | |
| JP | 2004-271330 A | 9/2004 | |
| JP | 2004-271331 A | 9/2004 | |
| JP | 2005-156234 A | 6/2005 | |
| JP | 2005-265758 A | 9/2005 | |
| JP | 2005-539242 A | 12/2005 | |
| JP | 2006-133001 A | 5/2006 | |
| JP | 2007-132837 A | 5/2007 | |
| WO | WO 02/055653 A1 | 7/2002 | |
| WO | WO 02/099408 A1 | 12/2002 | |
| WO | WO 03/016555 A1 | 2/2003 | |
| WO | WO 2004/038409 A2 | 5/2004 | |
| WO | WO-2004038410 A1 | 5/2004 | |
| WO | WO 2006/022092 A1 | 3/2006 | |
| WO | WO 2007/072790 A1 | 6/2007 | |

OTHER PUBLICATIONS

Bauer et al., "Laser micro-joining of dissimilar and biocompatable materials", Aug. 17, 2004, Proc. SPIE, vol. 5339, pp. 454-464.*

Japanese Office Action for Application No. 2003-392220, Oct. 27, 2009, Panasonic Corporation.

Japanese Office Action for JP 2006-186411, Nov. 17, 2009.

Niels Fertig et al., Activity of single ion channel proteins detected with a planar microstructure, Applied Physics Letters, Dec. 16, 2002, pp. 4865-4867, vol. 81, No. 25, 2002 American Institute of Physics.

James L. Rae et al., Patch Clamp Recordings from the Epithelium of the Lens obtained using Gasses selected for Low Noise and Improved Sealing Properties, Biophysical Society, Jan. 1984, pp. 144-146.

Bonnie L. Gray et al., Microchannel Platform for the Study of Endothelial Cell Shape and Function Biomedical Microdevices, Feb. 2002, pp. 9-16.

Japanese Office Action for Application No. 2010-186807, Mar. 29, 2011, Panasonic Corporation.

European Application Serial No. 05765636.5, Extended European Search Report mailed Jan. 30, 2012, 5 pgs.

* cited by examiner

FIG. 11 ered, so that cell 107 can be trapped in an opening
DEVICE FOR CELLULAR ELECTROPHYSIOLOGY SENSOR, CELLULAR ELECTROPHYSIOLOGY SENSOR USING THE DEVICE, AND METHOD FOR MANUFACTURING THE CELLULAR ELECTROPHYSIOLOGY SENSOR DEVICE This application is a U.S. NATIONAL PHASE APPLICATION OF PCT INTERNATIONAL APPLICATION PCT/JP2007/062887.

TECHNICAL FIELD

The present invention relates to a cell electrophysiological sensor device for measuring a cell electrophysiological phenomenon such as intracellular potential or extracellular potential, which is used for measuring physico-chemical change generated by cellular activities; a cell electrophysiological sensor using the same; and a method for manufacturing a cell electrophysiological sensor device.

BACKGROUND ART

A patch clamp technique in electrophysiology is known as a method for measuring an ion channel which the cell membrane possesses. With this patch clamp technique, various functions of the ion channel have been elucidated. The function of the ion channel has been a great interest and applied to development of drugs.

However, on the other hand, since the patch clamp technique as a measuring technique requires an extremely high skill of inserting a fine micropipette into a single cell with a high accuracy, this technique requires a skilled operator. Therefore, this technique is not suitable for an application that requires high-throughput measurement.

Therefore, an automated system, which does not require the insertion of a micropipette into an individual cell and is capable of automatically fixing a cell for measurement only by reducing pressure, has been developing.

Figure 11:
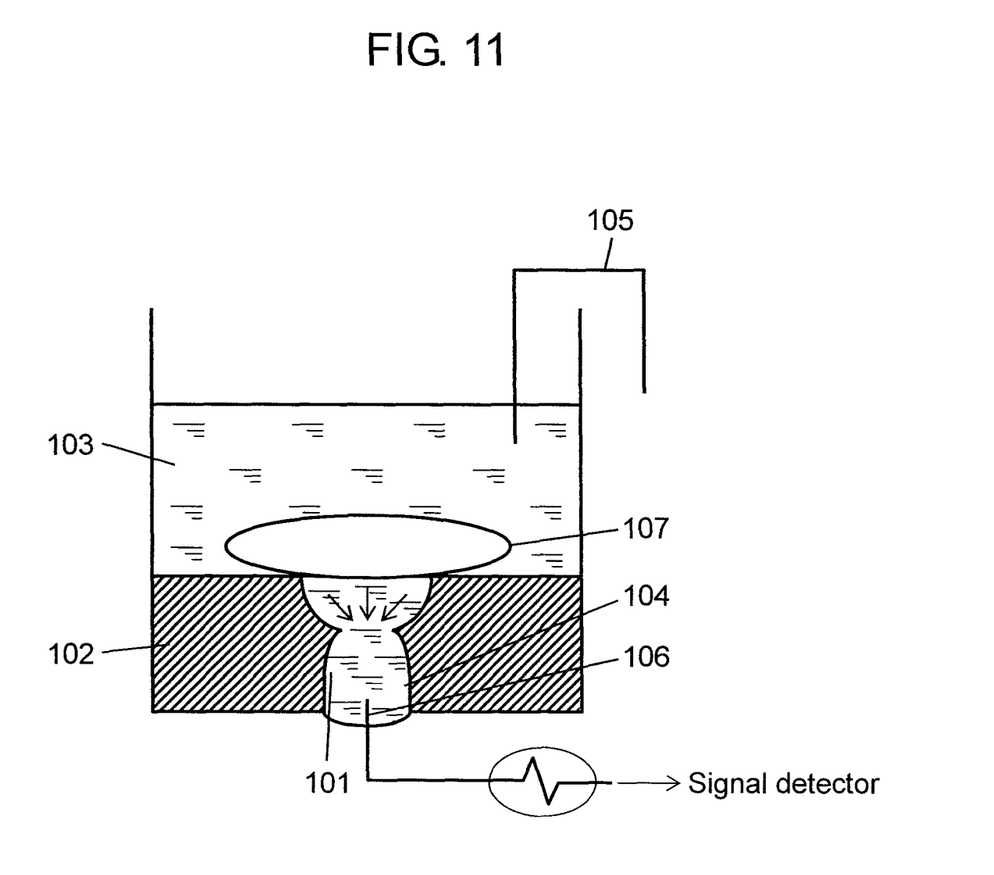
FIG. 11 is a sectional view showing a conventional cell electrophysiological sensor device.

FIG. 11 is a sectional view showing a conventional cell electrophysiological sensor. A conventional cell electrophysiological sensor includes sensor chip 102 having continuity hole 101, electrolytic baths 103 and 104 defined by sensor chip 102, and electrodes 105 and 106 disposed in electrolytic baths 103 and 104, respectively.

In this cell electrophysiological sensor, cell 107 and an electrolytic solution are filled in electrolytic bath 103, and the electrolytic solution is sucked by applying pressure from the upper part or reducing pressure from the lower part of continuity hole 101, so that cell 107 can be trapped in an opening of continuity hole 101. Then, for example, a drug is applied from the upper part of cell 107, and the potential difference between electrolytic baths 103 and 104 is measured by electrodes 105 and 106 and analyzed. Thus, the pharmacological reaction of cell 107 can be determined.

Then, such an extremely small sensor chip 102 is inserted into a chip holding part (not shown) such as a plate and a tube and then fixed with an adhesive agent and the like, which can be used as a cell electrophysiological sensor device.

Note here that examples similar to the above-mentioned conventional technology are described in the following patent documents.

However, as mentioned above, in the cell electrophysiological sensor device in which sensor chip 102 is inserted into the chip holding part, a leakage current tends to occur on the side surface of sensor chip 102.

The reason is because the airtightness between the side surface of sensor chip 102 and the chip holding part is low.

That is to say, when sensor chip 102 is joined to the chip holding part with an adhesive agent, unevenness and peeling easily occur in joining. Therefore, the airtightness between sensor chip 102 and the chip holding part becomes low. As a result, a leakage current tends to occur.

[Patent Document 1] Japanese Translation of PCT Publication No. 2002-518678
[Patent Document 2] Japanese Translation of PCT Publication No. 2003-527581

SUMMARY OF THE INVENTION

The present invention reduces a leakage current on a side surface of a sensor chip.

In order to do so, the present invention includes a sensor chip having a continuity hole and a chip holding part covering a side surface of the sensor chip. The sensor chip includes silicon as a main component, and the chip holding part is made of glass. This chip holding part is adhesively bonded to the side surface of the sensor chip by glass welding.

Thus, the present invention can reduce a leakage current on the side surface of the sensor chip.

The reason therefor is because the airtightness between the side surface of the sensor chip and the chip holding part is increased. That is to say, since the sensor chip made of silicon and the chip holding part made of glass are adhesively bonded to each other, the side surface of the sensor chip and the chip holding part can be brought into close contact with each other, and thus the joining is strengthened.

Therefore, the airtightness between the side surface of the sensor chip and the chip holding part is increased, resulting in reducing a leakage current.

REFERENCE MARKS IN THE DRAWINGS 1 well plate
2 holding plate
3 flow passage plate
4 sensor chip
5 through hole (electrolytic bath)
6 through hole
7 flow passage (electrolytic bath)
8 electrode
9 electrode
10 inlet port
11 outlet port
12 chip holding part
13 through hole (electrolytic bath)
14 continuity hole
15 thin plate
16 frame body
17 concave and convex parts
18A single crystal silicon layer
18B silicon dioxide layer
19 substrate
20A, 20B resist mask
21 mask hole
22 groove
23 mask hole
24 mask hole
25 curved surface
26 adhesive agent
27 extracellular fluid
28 intracellular fluid
29 cell
30 hydrophilic film
31 socket
32 opening

DETAILED DESCRIPTION OF THE PREFERRED EMBODIMENTS (First Exemplary Embodiment)

Figure 1:
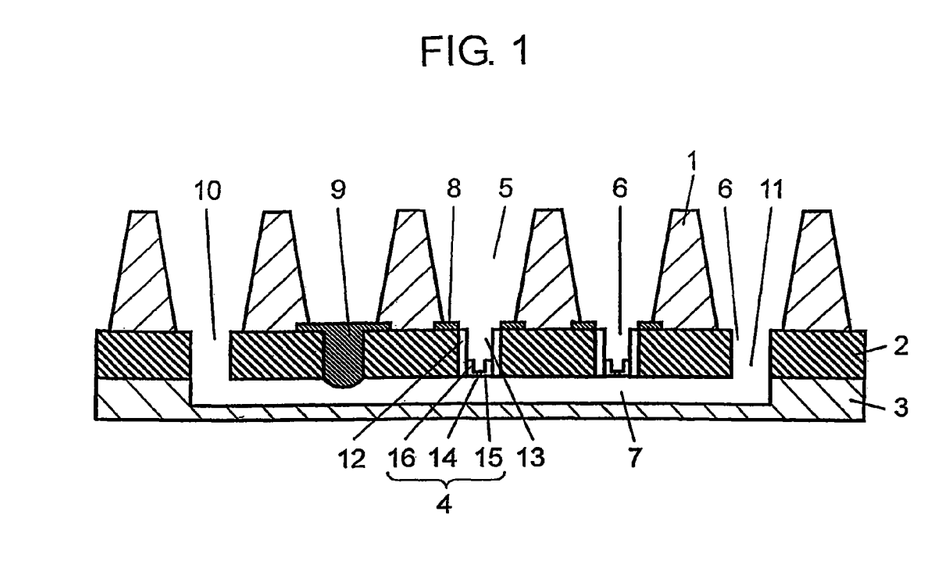
FIG. 1 is a sectional view showing a cell electrophysiological sensor in accordance with a first exemplary embodiment of the present invention.

FIG. 1 is a sectional view showing a cell electrophysiological sensor in accordance with a first exemplary embodiment of the present invention.

As shown in FIG. 1, the cell electrophysiological sensor in accordance with the first exemplary embodiment includes well plate 1, holding plate 2 that is brought into contact with the lower part of well plate 1, and flow passage plate 3 that is brought into contact with the lower part of holding plate 2. The below mentioned sensor chip 4 is mounted on holding plate 2.

Through hole 5 formed in well plate 1, through hole 6 formed in holding plate 2 and hollow space as flow passage 7 formed in flow passage plate 3 communicate with each other.

Furthermore, through hole 5 of well plate 1 functions as an electrolytic bath and can store an electrolytic solution such as extracellular fluid Furthermore, flow passage 7 of flow passage plate 3 also functions as an electrolytic bath and can store an electrolytic solution such as intracellular fluid.

In holding plate 2, electrodes 8 and 9 are provided on the surface of holding plate 2 and a part of the inside of through hole 6. Electrodes 8 and 9 can be electrically connected to the liquid filled in through hole 5 and flow passage 7.

Electrodes 8 and 9 can be used to measure electrical parameters such as electric potential and electric current generated by an electrophysiological phenomenon of cells. Note here that the shapes, positions to be disposed and materials of electrodes 8 and 9 are not necessarily limited to the examples in this exemplary embodiment.

Furthermore, parts of through holes 6 of holding plate 2 function as inlet port 10 and outlet port 11 for an electrolytic solution to be filled into flow passage 7 (electrolytic bath).

Furthermore, the cell electrophysiological sensor device in accordance with this exemplary embodiment includes cylindrical-shaped chip holding part 12 inserted into through hole 6 of plate-shaped holding plate 2, and sensor chip 4 inserted into the inside of through hole 13 of chip holding part 12. That is to say, chip holding part 12 of this exemplary embodiment is a cylindrical shape in which the inner diameter (dimension) of through hole 13 is somewhat larger than the outer diameter (dimension) of sensor chip 4, and the side surface of sensor chip 4 is covered with chip holding part 12. Sensor chip 4 has one or a plurality of continuity holes 14. Sensor chip 4 includes silicon as a main component, and, in this exemplary embodiment, it is formed of a single crystal silicon layer and a silicon dioxide layer.

Furthermore, chip holding part 12 is made of glass such as borosilicate glass having an excellent hydrophilic property. Chip holding part 12 is bonded to the side surface of sensor chip 4 by glass-welding.

Herein, sensor chip 4 in this exemplary embodiment includes disk-shaped thin plate 15 having a thickness of 10 μm to 100 μm and cylindrical-shaped frame body 16 formed on the upper surface of thin plate 15. Continuity hole 14, formed on thin plate 15 and having a diameter (dimension) of 1 to 3 μmφ, penetrates thin plate 15 from the upper surface to the lower surface. Note here that the opening diameter of continuity hole 14 suitable for holding a cell is not larger than 5 μm. Furthermore, the number of continuity holes 14 is not necessarily limited to one, and a plurality of continuity holes 14 may be provided.

Figure 2:
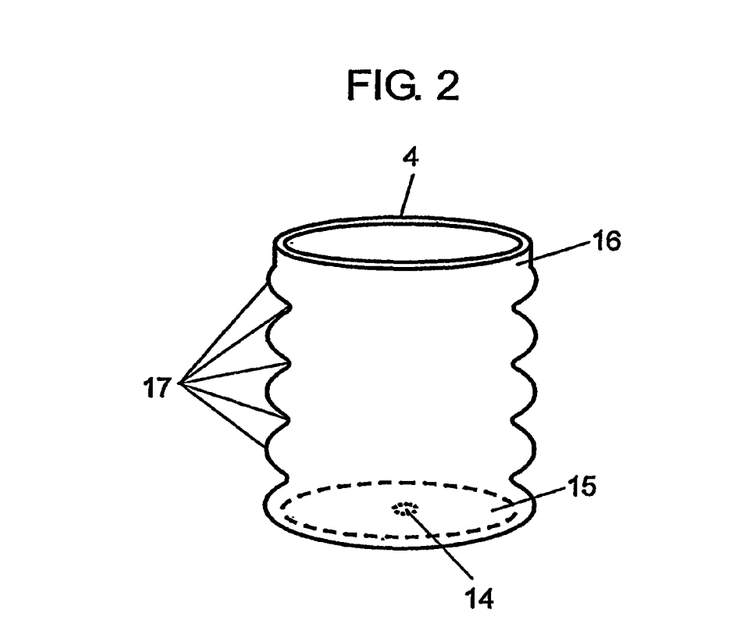
FIG. 2 is a perspective view showing a sensor chip in accordance with the first exemplary embodiment of the present invention.

FIG. 2 is a perspective view showing a sensor chip in accordance with the first exemplary embodiment of the present invention.

As shown in FIG. 2, annular concave and convex parts 17 are repeatedly formed as a laminate on the outer side surface of frame body 16 in the horizontal direction that is the same direction of thin plate 15.

Furthermore, sensor chip 4 of this exemplary embodiment is treated so that the side surface of frame body 16 has a hydrophilic property.

Next, materials of members of the cell electrophysiological sensor of the first exemplary embodiment are described.

Well plate 1, holding plate 2 and flow passage plate 3 are made of resin, more preferably, thermoplastic resin. Thus, a highly homogeneous molded product can be obtained from these materials with high productivity by using, for example, an injection molding method. More preferably, the thermoplastic resin is any one of polycarbonate (PC), polyethylene (PE), olefin polymer, and poly(methyl methacrylate) (PMMA), or the combination thereof. Holding plate 2 made of these materials can be easily joined to chip holding part 12 made of glass having an excellent hydrophilic property by using an ultraviolet curing adhesive agent. It is further preferable from the viewpoint of workability, production cost, and availability of materials that the thermoplastic resin is cyclic olefin polymer, linear olefin polymer, or cyclic olefin copolymer obtained by polymerizing these polymers, or polyethylene (PE).

In particular, since the cyclic olefin copolymer has high transparency and high resistance to alkaline and acidic inorganic agents, it is suitable for the manufacturing method and use environment of the present invention. Furthermore, since these materials transmit ultraviolet rays, they exhibit the effect when an ultraviolet curing adhesive agent is used.

Note here that when holding plate 2 is produced integrally with a silicon substrate and sensor chip 4 is integrated with a part of holding plate 2, cost is increased and a yield is deteriorated. Furthermore, when defective sensor chip 4 is included in part, it cannot be repaired.

On the contrary, when holding plate 2 of the first exemplary embodiment is made of the above-mentioned resin, extremely small sensor chips 4 are produced efficiently at one time and only non-defective chips are selected and used, so that a cell electrophysiological sensor with high yield can be realized and a configuration having repairability can be realized.

Then, it is important that the internal wall surface of the through hole of chip holding part 12 in the first exemplary embodiment is hydrophilic. That is to say, it is desirable that chip holding part 12 is made of glass having a contact angle with respect to water of not less than 0° and not more than 10°.

Therefore, it is preferable that the material of chip holding part 12 is glass containing silicon dioxide. An example of the material includes borosilicate glass (for example, Corning: #7052, #7056), aluminosilicate glass or lead borosilicate glass (for example, Corning: #8161), or the like. Note here that the contact angle with respect to water refers to an angle made by the surface of a water droplet and the surface of a solid in a state in which the water droplet of pure water is put on the solid surface and they reach equilibrium. In general, the contact angle can be measured by a θ/2 method. With the method, the contact angle is obtained from an angle of a line linking left and right end points to the top of the water droplet with respect to the surface of the solid. Alternatively, the angle can be measured by using a protractor, and the like.

Furthermore, the softening point of glass is important from the viewpoint of workability. It is preferable that a temperature suitable for glass-welding to the side surfaces of sensor chip 4 is not less than the softening point of glass. More preferably the temperature is in the range from 500° C. to 900° C. The use of glass having a softening point of less than 500° C. makes the intensity insufficient, and the use of glass having a softening point of more than 900° C. deteriorates workability.

Next, a method for manufacturing a cell electrophysiological sensor in accordance with this exemplary embodiment is described.

FIGS. 3A to 3E are sectional views showing each step of a manufacturing process of sensor chip 4 in accordance with the first exemplary embodiment of the present invention.

Figure 3A:
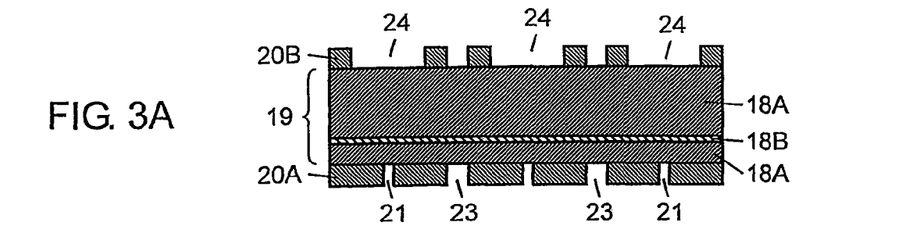
FIG. 3A is a sectional view showing a first step of a manufacturing process of the sensor chip in accordance with the first exemplary embodiment of the present invention.

Firstly, as shown in FIG. 3A, SOI substrate 19 including single crystal silicon layers 18A and thin silicon dioxide layer 18B having a thickness of about 2 μm is provided, resist mask 20A is disposed on the lower surface of substrate 19 and resist mask 20B is disposed on the upper surface of substrate 19. Herein, resist mask 20A is provided with mask hole 21 having substantially the same shape as that of the opening of continuity hole 14 in a part corresponding to continuity hole 14 and mask hole 23 for providing a groove for separation (groove 22 shown in FIG. 3C). On the other hand, resist mask 20B is provided with mask hole 24 on the surface of a part other than a part corresponding to frame body 16.

Figure 3B:
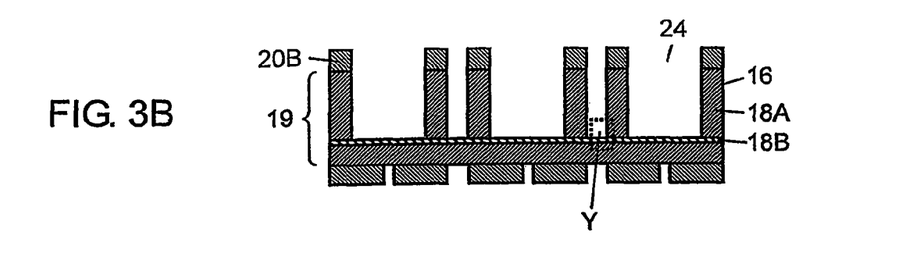
FIG. 3B is a sectional view showing a second step of a manufacturing process of the sensor chip in accordance with the first exemplary embodiment of the present invention.

Next, as shown in FIG. 3B, substrate 19 is etched from the upper surface thereof to silicon dioxide layer 18B by dry etching mentioned below so as to form frame body 16.

Figure 3C:
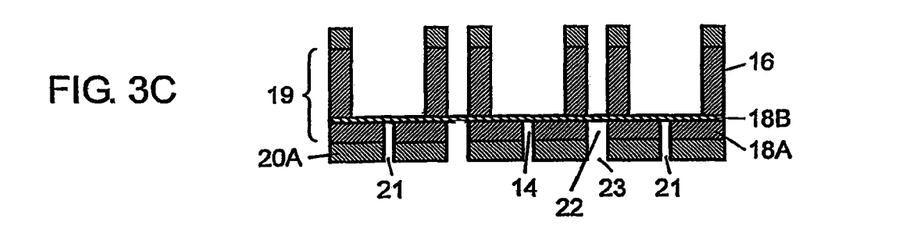
FIG. 3C is a sectional view showing a third step of a manufacturing process of the sensor chip in accordance with the first exemplary embodiment of the present invention.

Then, as shown in FIG. 3C, substrate 19 is etched from the lower surface thereof to silicon dioxide layer 18B so as to form continuity hole 14 and groove 22 for separation.

Figure 3D:
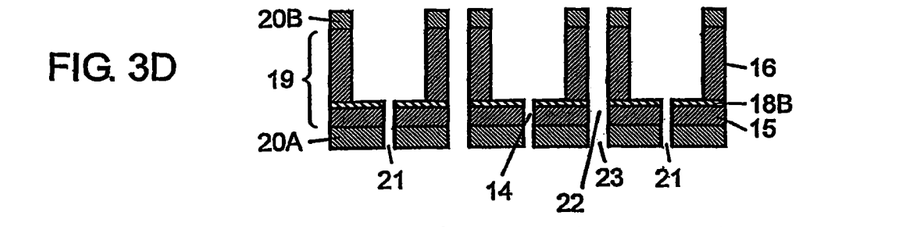
FIG. 3D is a sectional view showing a fourth step of a manufacturing process of the sensor chip in accordance with the first exemplary embodiment of the present invention.

Next, as shown in FIG. 3D, silicon dioxide layer 18B located above continuity hole 14 and groove 22 is etched and removed by using gas for etching only silicon dioxide, for example, mixture gas of Ar and $CF_4$, so that sensor chip 4 is separated into individual pieces.

Figure 3E:
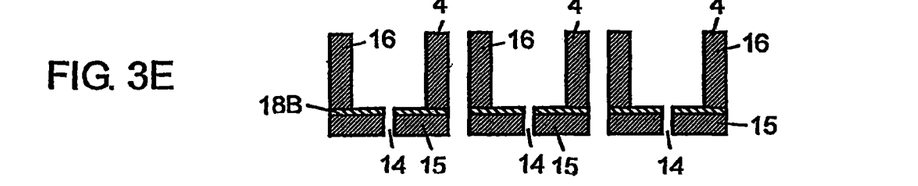
FIG. 3E is a sectional view showing a fifth step of a manufacturing process of the sensor chip in accordance with the first exemplary embodiment of the present invention.

Then, as shown in FIG. 3E, resist masks 20A and 20B are removed. Thus, sensor chip 4 including frame body 16 and thin plate 15 is completed. In this exemplary embodiment, frame body 16 is formed earlier than thin plate 15. The manufacturing order may be opposite. When thin plate 15 is formed earlier than frame body 16, it is possible to suppress the breakage of the thin plate during processing of continuity hole 14.

Herein, the above-mentioned dry etching process is described in detail.

In this dry etching process, gas for promoting etching (hereinafter, referred to as "promoting gas") and gas for suppressing etching (hereinafter, referred to as "suppressing gas") are used. In the first exemplary embodiment, $SF_6$ is used as the promoting gas and $C_4F_8$ is used as the suppressing gas.

Firstly, plasma is generated above substrate 19 by an inductive coupling method of external coil, into which $SF_6$ as the etching gas is introduced. Then, F radical is generated.

Then, the F radical reacts with substrate 19, so that substrate 19 is chemically etched.

At this time, when a high frequency is applied to substrate 19, a negative bias voltage is generated on substrate 19. Then, positive ions ($SF_5^+$) contained in the etching gas collides vertically with respect to substrate 19. Thus, substrate 19 is physically etched by this ion bombardment.

As a result, this dry etching proceeds in the vertical direction (downward) to the surface of substrate 19.

On the other hand, when the suppressing gas, $C_4F_8$, is used, a high frequency is not applied to substrate 19. Thus, no bias voltage is generated on substrate 19.

Therefore, $CF^+$ contained in $C_4F_8$ as the suppressing gas is attached to the wall surface of the hole by dry etching of substrate 19 without being biased. Thus, a homogeneous film is formed.

Then, the $CF^+$ film functions as a protective film to suppress etching. Herein, this protective film is formed not only on the wall surface but also on the bottom surface of a hole during processing. However, the protective film formed on the bottom surface can be easily removed by the above-mentioned ion bombardment as compared with the protective film formed on the wall surface. As a result, the etching proceeds downward.

Figure 4:
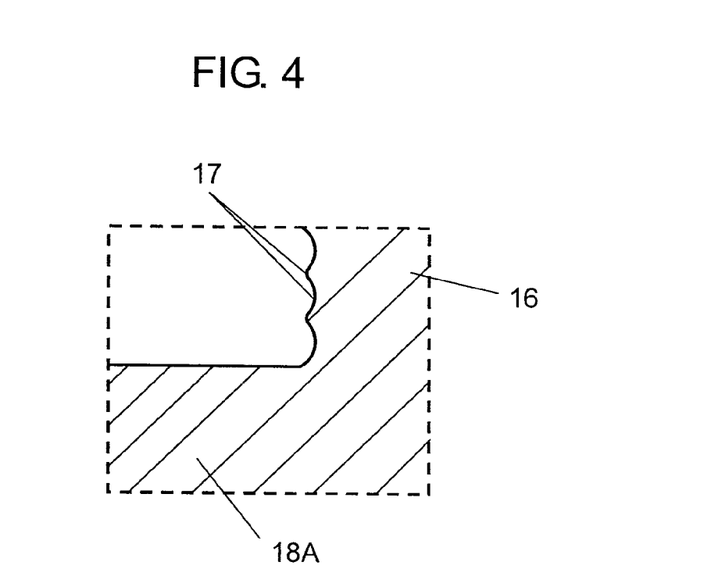
FIG. 4 is an enlarged sectional view showing a main part of the sensor chip in accordance with the first exemplary embodiment of the present invention.

However, as shown in the perspective view of sensor chip 4 in FIG. 2 and an enlarged sectional view showing a main part of sensor chip 4 in FIG. 4 (a sectional view enlarging the main part Y shown in FIG. 3B), depending upon the conditions such as the ratio of the promoting gas and the suppressing gas and the processing time, etching tends to proceed not only in the downward direction but also in the horizontal direction. On the side surface of sensor chip 4, concave and convex parts 17 in which annular concave and convex parts are formed as a laminate.

Next, hydrophilic treatment for allowing the side surface of sensor chip 4, that is, the side surface of frame body 16 to have hydrophilic property is carried out.

As the hydrophilic treatment suitable for the first exemplary embodiment, the side surface of frame body 16 is subjected to acidic and alkaline chemical treatment, for example, wet treatment with sulfuric acid, hydrogen peroxide, and the like, so as to decompose and remove organic matters containing a carbon atom, or subjected to physical treatment such as plasma irradiation or UV irradiation so as to decompose and remove organic matters, and then immersed in pure water in order to maintain the hydrophilic property.

Then, sensor chip 4 is inserted into through hole 13 of chip holding part 12. At this time, in the first exemplary embodiment, since sensor chip 4 is immersed in pure water in advance, the pure water is sufficiently attached to the surface of sensor chip 4 and filled in the inside of frame body 16. Furthermore, chip holding part 12 is made of hydrophilic glass. Therefore, sensor chip 4 of the first exemplary embodiment has an excellent affinity to chip holding part 12, it is easily brought into close contact with chip holding part 12, can be self-aligned uniformly on the position of chip holding part 12 shown in FIG. 1 due to the effect of the surface tension of water.

Furthermore, since the direction of sensor chip 4 does not affect the self-alignment property, it is known that sensor chip 4 is self-aligned along one surface of chip holding part 12 regardless of whether the surface of thin plate 15 is directed upward or downward.

Furthermore, it is preferable that a glass composition constituting chip holding part 12 includes silicon dioxide in order to improve the hydrophilic property.

Then, in order to allow sensor chip 4 to stand still in a predetermined position, sensor chip 4 and chip holding part 12 are fixed so that they become horizontal in the longitudinal direction, and then placed in, for example, a heat treatment furnace.

Note here that an example using a heat treatment furnace is described. However, welding can be carried out by local heating with the use of a heater, and the like, or by the local heating with the use of a near infrared laser so as to heat only the vicinity of sensor chip 4.

Then, the attached water is dried at 80° C. to 120° C., followed by heating to a predetermined temperature at which glass is welded so as to melt a glass composition in chip holding part 12. Then, the melted composition is allowed to attach to the entire side surface of sensor chip 4. In order to weld glass, glass is required to be heated to at least not less than a glass softening point of the glass to be used. From the viewpoint of workability, the temperature is preferably not more than 900° C. In the first exemplary embodiment, since borosilicate glass (for example, Corning: #7052, #7056) is employed for chip holding part 12, the optimal condition of thermal welding includes a temperature of 700° C. to 750° C. and a heating time of about 10 seconds. At this time, covalent bonding between chip holding part 12 and the side surface of sensor chip 4 proceeds and the joining strength is improved as the temperature becomes higher in the appropriate temperature range.

Then, it is preferable that the above-mentioned drying treatment and joining treatment by heat welding are carried out at one time. This is because displacement between sensor chip 4 and chip holding part 12 can be prevented when they are carried out at one time.

At this time, it is confirmed that the side surface of sensor chip 4 and chip holding part 12 can be joined to each other by glass welding when the gap between them is not more than 400 μm. The glass welding can be carried out efficiently when, for example, the outer diameter (dimension) of sensor chip 4 is made to be 700 μm, the inner diameter (dimension) and the outer diameter (dimension) of the through hole of chip holding part 12 are made to be 1.0 mm and 1.50 mm, respectively. At that time, the joining by the glass welding can be carried out under the heat treatment conditions in which the welding temperature is 718° C. and the welding time is not more than 10 seconds. The outer shape of chip holding part 12 may be any shape as long as chip holding part 12 can be fixed to and held by holding plate 2.

Figure 5:
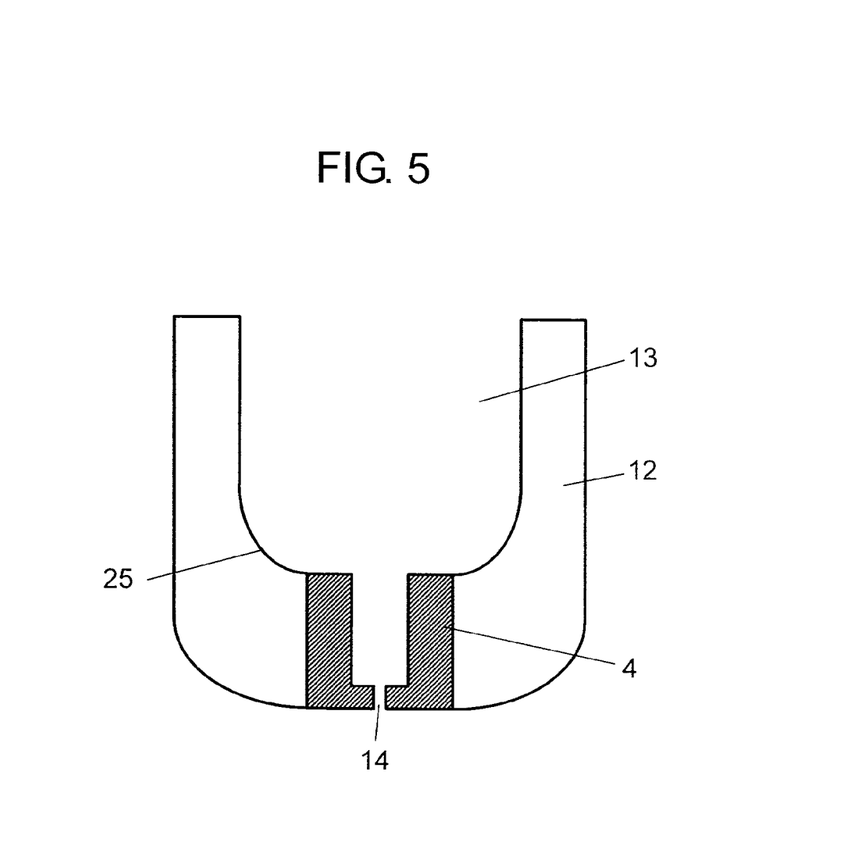
FIG. 5 is an enlarged sectional view showing a main part of a cell electrophysiological sensor device in accordance with the first exemplary embodiment of the present invention.

In the first exemplary embodiment, since the inner diameter (dimension) of through hole 13 of chip holding part 12 is larger than the outer diameter (dimension) of sensor chip 4, when heating is carried out at temperatures of not less than the glass softening point, a glass component in chip holding part 12 melts so as to increase the density, and stick to the side surface of sensor chip 4 when it is contracted. Therefore, in the first exemplary embodiment, as shown in FIG. 5, the inner wall of through hole 13 of chip holding part 12 has curved surface 25 communicating with the upper surface of sensor chip 4.

Then, as mentioned above, after the side surface of sensor chip 4 and chip holding part 12 are glass-welded, cylindrical-shaped chip holding part 12 is cut into a predetermined size and separated into individual pieces. By repeating such operations, a plurality of separated chips (separated chip holding part 12) can be produced.

Note here that chip holding part 12 may be cut into a predetermined size and aligned in advance, and sensor chip 4 may be then inserted into the aligned chip holding part 12.

Meanwhile, on the entire surface of holding plate 2 shown in FIG. 1, electrode 8 is formed by pressing or vacuum evaporation. Then, through hole 6, which penetrates holding plate 2 from the upper surface to the lower surface, is formed by using a twist drill in a position into which chip holding part 12 is inserted. Thereafter, the above-mentioned electrode 8 is patterned by photolithography and a mixture of Ag and AgCl is dispensed or printed so as to form electrode 9 inside a part of through hole 6. Note here that drill punching and patterning may be carried out in the opposite order.

Figure 6:
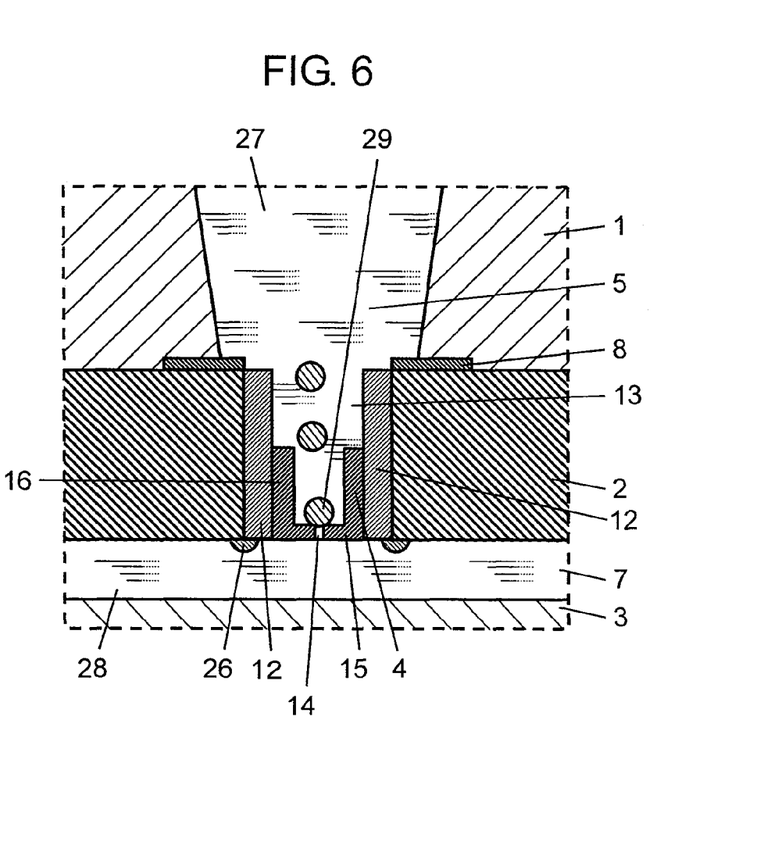
FIG. 6 is a partial sectional view showing the cell electrophysiological sensor in accordance with the first exemplary embodiment of the present invention.

Next, chip holding part 12 integrated with sensor chip 4 is inserted into through hole 6 of holding plate 2. At this time, for example, holding plate 2 and chip holding part 12 can be joined to each other with adhesive agent 26, and the like, as shown in FIG. 6. From the viewpoint of workability, it is preferable that ultraviolet curing resin is used as adhesive agent 26.

Thereafter, as shown in FIG. 1, holding plate 2 and well plate 1 are adhesively bonded to each other as well as holding plate 2 and flow passage plate 3 are adhesively bonded to each other. A preferable example of the joining method includes joining by thermal welding using a laser, or joining with an ultraviolet curing adhesive agent by irradiation with ultraviolet ray.

Note here that well plate 1 and flow passage plate 3 can be joined to holding plate 2 simultaneously. Any of the methods can be appropriately employed.

An operation of the cell electrophysiological sensor in accordance with the first exemplary embodiment is described.

Firstly, as shown in FIG. 6, extracellular fluid 27 is stored in through hole 5 (electrolytic bath) of well plate 1 and through hole 13 (electrolytic bath) of chip holding part 12, and intracellular fluid 28 is filled in flow passage 7 (electrolytic bath) of flow passage plate 3 by sucking intracellular fluid 28 from inlet port 10 to outlet port 11 of well plate 1. Herein, extracellular fluid 27 is typically an electrolytic solution supplemented with 155 mM of $K^+$ ion, about 12 mM of $Na^+$ ion, and about 4.2 mM of $Cl^-$ ion in the case of, for example, mammalian muscle cells. Intracellular fluid 28 is an electrolytic solution supplemented with about 4 mM of $K^+$ ion, about 145 mM of $Na^+$ ion, and about 123 mM of $Cl^-$ ion.

In this state, between electrode 8 electrically connected to extracellular fluid 27 in through hole 5 of well plate 1 and through hole 13 of chip holding part 12 and electrode 9 electrically connected to extracellular fluid 28 in flow passage 7, conductive resistance value of about 100 kΩ to 10 MΩ can be observed. This is because intracellular fluid 28 or 27 penetrates via continuity hole 14, so that an electric circuit is formed between two electrodes 8 and 9.

Next, cells 29 are put from the side of cell plate 1.

Then, when the pressure of one of inlet port 10 and outlet port 11 of well plate 1 is reduced, cell 29 is attracted to the opening of continuity hole 14 to block the opening of continuity hole 14. Thereby, the electric resistance between through holes 5 at the side of well plate 1 and through hole 13 of chip holding part 12 and the side of flow passage 7 becomes a sufficiently high resistance as GΩ or more (this state is referred to as "giga seal"). In this giga seal state, when the intracellular potential and extracellular potential change due to the electrophysiological activity of cell 29, only a slight potential difference or change of the electric current can be measured with a high accuracy.

Hereinafter, an effect of the first exemplary embodiment is described.

In the first exemplary embodiment, a leakage current on the side surface of sensor chip 4 can be reduced.

This is because the airtightness between the side surface of sensor chip 4 and chip holding part 12 is increased.

Herein, for example, when sensor chip 4 and chip holding part 12 are joined with an adhesive agent, it is extremely difficult to apply the adhesive agent on the entire side surface of sensor chip 4. Furthermore, the joining with an adhesive agent exhibits low adhesive strength and peels easily.

On the contrary, in the first exemplary embodiment, since sensor chip 4 including silicon as a main component and chip holding part 12 made of glass are adhesively bonded to each other by glass welding, chip holding part 12 can be strongly joined to substantially entire side surface of sensor chip 4.

Accordingly, the airtightness between the side surface of sensor chip 4 and chip holding part 12 is increased, and liquid leakage and the like can be suppressed. As a result, a leakage current can be reduced.

Note here that since the liquid leakage in the vicinity of sensor chip 4 has an important effect on the property of the giga seal, the structure capable of reliably preventing a liquid leakage on the outer surface of sensor chip 4 is extremely important as a structure of the cell electrophysiological sensor. Furthermore, the structure also has a large effect on the measurement accuracy of the cell electrophysiological sensor.

Furthermore, in this exemplary embodiment, since sensor chip 4 is configured by thin plate 15 and frame body 16, even if the depth of continuity hole 14 is small, by increasing the thickness or length of frame body 16, handling of sensor chip 4 can be facilitated.

Furthermore, in the first exemplary embodiment, since thin plate 15 has a disk shape and frame body 16 has a cylindrical shape, the stress from chip holding part 12 can be dispersed so as to suppress damage. Furthermore, through hole 13 of chip holding part 12 may have a circular cross section, which facilitates punching. Furthermore, since through hole 13 is not directional, sensor chip 4 can be easily inserted into through hole 13.

Furthermore, in the first exemplary embodiment, as shown in FIG. 5, since the inner wall of through hole 13 of chip holding part 12 has curved surface 25 communicating with the upper surface of sensor chip 4, the fluidity of a solution from through hole 13 to the opening of continuity hole 14 is improved. This makes it easy to trap a cell in the opening of continuity hole 14, thus contributing the measurement accuracy of the cell electrophysiological sensor.

Furthermore, in the first exemplary embodiment, since chip holding part 12 uses glass containing silicon dioxide, having a contact angle with respect to water of not less than 0° and not more than 10°, and having excellent hydrophilic property, and since the side surface of sensor chip 4 is made to be hydrophilic, the adhesiveness between chip holding part 12 and side surface of sensor chip 4 is improved. Thus, chip holding part 12 and side surface of sensor chip 4 can be joined to each other by glass welding.

In particular, since chip holding part 12 has a cylindrical shape, it is easily deformed due to heating. Therefore, when the gap between the inner wall of through hole 13 of chip holding part 12 and side surface of sensor chip 4 is not more than 400 μm, joining by welding can be reliably carried out in the glass welding process.

Note here that the inner wall of through hole 13 of chip holding part 12 may be chemically or physically treated so as to improve the hydrophilic property or a hydrophilic film made of different compositions may be formed.

Furthermore, in the first exemplary embodiment, sensor chip 4 is formed and then immersed in water, so that sensor chip 4 is inserted into through hole 13 of chip holding part 12 more easily as compared with the case sensor chip 4 is inserted in a dry state because static electricity does not easily occur.

Furthermore, in the first exemplary embodiment, as shown in FIG. 2, annular concave and convex parts 17 are formed repeatedly as a laminate on the outer side surface of frame body 16 of sensor chip 4. Therefore, contact resistance is increased in the interface between the side surface of sensor chip 4 and the inner wall of through hole 13 of chip holding part 12, thus suppressing slipping of sensor chip 4 from through hole 13.

This configuration is particularly effective because sensor chip 4 can be provisionally fixed to a predetermined position prior to process of glass welding.

Furthermore, by forming concave and convex parts 17 in the horizontal direction of sensor chip 4, concave and convex parts 17 are perpendicular to the gravity applied to sensor chip 4 itself. Therefore, it is possible to further increase the contact resistance by concave and convex parts 17, thus strengthening the joining strength.

In addition, in the first exemplary embodiment, since concave and convex parts 17 are formed so as to form a laminate of annular concave and convex parts along the outer peripheral shape of the outer side surface of sensor chip 4, it is possible to suppress the entry of an electrolytic solution into the gap between sensor chip 4 and through hole 13 of chip holding part 12.

That is to say, depending upon shapes of concave and convex parts 17, an electrolytic solution enters the gap between the side surface of sensor chip 4 and chip holding part 12, and a leakage current may occur. In the first exemplary embodiment, however, since concave and convex parts 17 are formed in an annular shape, a plurality of gaps formed by concave parts are appropriately blocked by the convex parts adjacent to the concave parts. As a result, it is possible to suppress the entry of an electrolytic solution into the gap.

Furthermore, in the first exemplary embodiment, very small sensor chip 4 may be inserted into a relatively large chip holding part 12 and then fixed to holding plate 2, which facilitates handling and assembly.

Furthermore, sensor chip 4, chip holding part 12 and holding plate 2 are produced separately and then chip holding part 12 is fitted into through hole 6 of holding plate 2 and joined together. Thus, a cell electrophysiological sensor can be produced efficiently. Furthermore, when defective sensor chip 4 is included, it can be replaced easily.

In addition, in the method in which sensor chip 4 made of hydrophobic silicon is inserted into through hole 6 of holding plate 2 directly, sensor chip 4 may be scattered due to static electricity, thus deteriorating workability. Furthermore, position into which sensor chip 4 is inserted becomes inconsistent, and much time is required for arrangement. On the contrary, in the first exemplary embodiment, highly hydrophilic chip holding part 12 is inserted into through hole 6 of holding plate 2, thereby facilitating the positioning of sensor chip 4 and improving the workability. Furthermore, sensor chip 4 made of hydrophobic silicon and holding plate 2 made of hydrophobic resin are not brought into contact with each other, and chip holding part 12 made of hydrophilic glass is inserted therebetween. Thereby, it is possible to suppress the generation of foams, resulting in enabling the measurement accuracy of the cell electrophysiological sensor to be improved.

Note here that in the first exemplary embodiment, sensor chip 4 includes thin plate 15 and frame body 16. However, it may be a plate-shaped product. Furthermore, in the first exemplary embodiment, frame body 16 is formed in the upper surface side of thin plate 15. However, frame body 16 may be formed in the lower surface side of thin plate 15.

Figure 7:
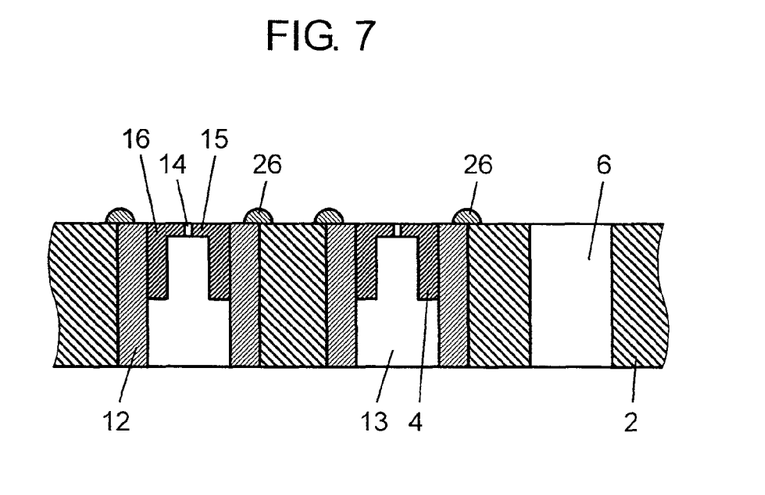
FIG. 7 is a sectional view showing another example of a cell electrophysiological sensor in accordance with the first exemplary embodiment of the present invention.

Furthermore, in the first exemplary embodiment, sensor chip 4 is fixed to the lower end part of chip holding part 12. However, as shown in FIG. 7, sensor chip 4 may be fixed to the upper end part of chip holding part 12. Thus, an electrolytic solution at the upper side can be easily sucked from the lower part of sensor chip 4 in the state in which an electrolytic solution is filled in the electrolytic baths located in both upper and lower parts of sensor chip 4. Thus, a cell can be trapped in the opening of continuity hole 14. Furthermore, sensor chip 4 may be fixed in the middle part of chip holding part 12. Such selections should be suitably determined depending upon the nature of the cell to be measured.

Furthermore, when sensor chip 4 is disposed on the upper end of chip holding part 12, the inner wall of through hole 13 of chip holding part 12 can be configured to have a curved surface communicating with the lower surface of sensor chip 4. Furthermore, when sensor chip 4 is disposed in the middle part of chip holding part 12, the inner wall of through hole 13 of chip holding part 12 can be configured to have a curved surface communicating with the upper and lower surfaces of sensor chip 4. In any case, the fluidity of a solution between electrolytic baths disposed in the upper and lower parts of continuity hole 14 is improved.

In addition, in the first exemplary embodiment, chip holding part 12 is inserted into holding plate 2. Thus, a plurality of sensor chips 4 can be mounted on one substrate. However, holding plate 2 may not be necessarily used.

Furthermore, when ultraviolet ray transmitting glass having an average ultraviolet ray transmittance of not less than 70% and less than 100% in the wavelength range from 380 nm to 340 nm is used as chip holding part 12, holding plate 2 and chip holding part 12 can be adhesively bonded to each other easily with adhesive agent 26 made of ultraviolet curing resin.

Furthermore, when well plate 1, holding plate 2 and flow passage plate 3 are made of ultraviolet ray transmitting resin and joined to each other with an adhesive agent made of ultraviolet curing resin, the ultraviolet ray can be allowed to reach the joined interface regardless of the direction of irradiation with ultraviolet ray. Therefore, the efficiency of joining is improved.

Furthermore, as shown in FIG. 1, the inner wall of through hole 5 of well plate 1 as an electrolytic bath is tapered so that it widened from the lower part to the upper part. Thus, an electrolytic solution and cells can be easily filled in.

Note here that sensor chip 4 may be formed of single crystal silicon substrate. However, as shown in the first exemplary embodiment, sensor chip 4 is formed of a so-called SOI substrate (substrate 19 in FIG. 3) with the dimensions of thin plate 15 and frame body 16 can be determined with a high accuracy. Furthermore, silicon dioxide layer 18B between thin plate 15 and frame body 16 has high insulation and also can be made to have a high thickness. Therefore, a stray capacity component occurring between electrodes 8 and 9 can be reduced. As a result, the measurement accuracy of the cell electrophysiological sensor can be improved.

(Second Exemplary Embodiment)

Figure 8:
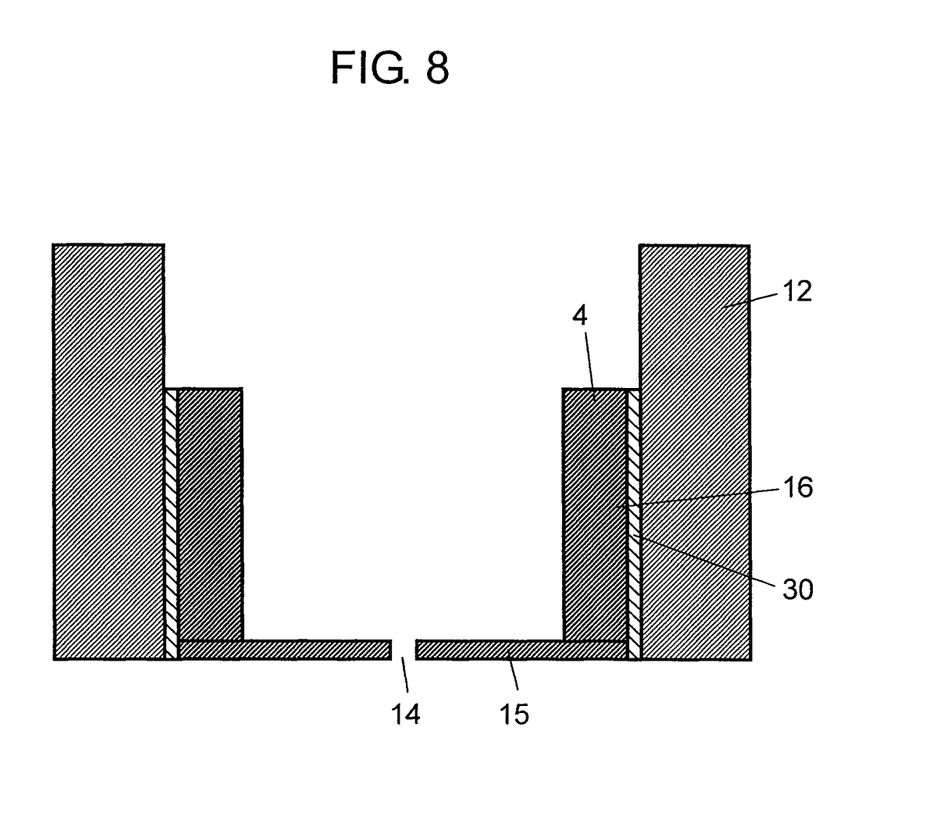
FIG. 8 is a partial sectional view showing a cell electrophysiological sensor in accordance with a second exemplary embodiment of the present invention.

FIG. 8 is a partial sectional view showing a cell electrophysiological sensor in accordance with a second exemplary embodiment of the present invention. The same reference numerals are given to the same configurations as in the first exemplary embodiment and the description thereof is omitted herein.

The second exemplary embodiment is different from the first exemplary embodiment in that hydrophilic film 30 is formed on the outer surface of sensor chip 4 by a thin film process in the second exemplary embodiment as shown in FIG. 8. In the second exemplary embodiment, hydrophilic film 30 is made of silicon dioxide.

Then, a method for forming hydrophilic film 30 includes a thin film process such as a method of thermally oxidizing the outer side surface of sensor chip 4, or a method of sputtering silicon dioxide, a CVD method, or the like. Then, by forming a film by using this thin film process, for example, hydrophilic film 30 having a thickness of 500 angstrom to 10 μm and made of silicon dioxide can be formed.

Hydrophilic film 30 can be also made of silicon oxide or silicon nitride other than silicon dioxide. Also in this case, a sputtering method or a CVD method can be employed.

Furthermore, it is preferable that the hydrophilic property of hydrophilic film 30 at that time is not more than 10° when it is expressed as a contact angle.

When such hydrophilic film 30 is formed, in the second exemplary embodiment, a wettability of the side surface of sensor chip 4 is improved and affinity with respect to the glass component of chip holding part 12 is further improved. Then, the melted glass component sufficiently infiltrates into the side surface of sensor chip 4, and the adhesiveness on the joining interface between sensor chip 4 and chip holding part 12 can be improved and peeling can be suppressed, resulting in reducing a leakage current.

Note here that in the second exemplary embodiment, since hydrophilic film 30 is made of an insulating silicon dioxide, the insulating property of the side surface of sensor chip 4 can be improved. Furthermore, since silicon dioxide can be covalently bonded to glass, when sensor chip 4 and chip holding part 12 are glass-welded to each other, by covalently bonding at least a part of hydrophilic film 30 and chip holding part 12 to each other, the joining strength can be further strengthened. As a result, the reliability of the cell electrophysiological sensor can be improved.

(Third Exemplary Embodiment)

Figure 9:
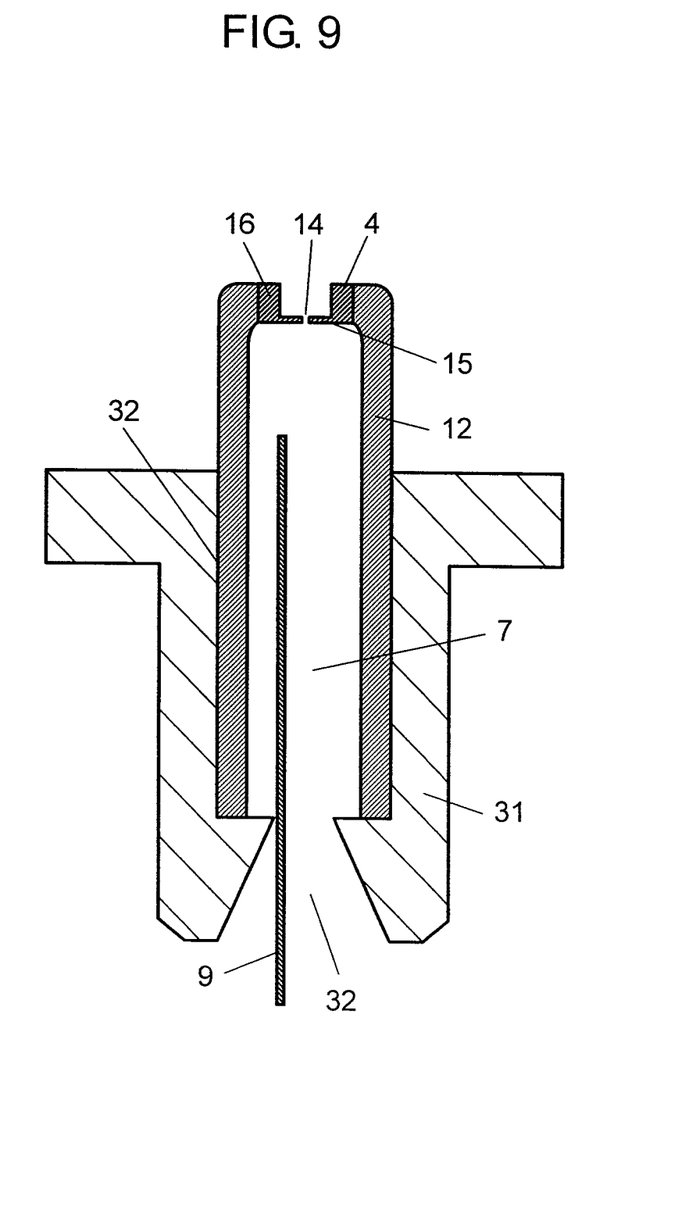
FIG. 9 is a partial sectional view showing a cell electrophysiological sensor in accordance with a third exemplary embodiment of the present invention.

FIG. 9 is a partial sectional view showing a cell electrophysiological sensor in accordance with a third exemplary embodiment of the present invention. The same reference numerals are given to the same configurations as in the first and second exemplary embodiments and the description thereof is omitted herein.

The third exemplary embodiment is different from the first exemplary embodiment in that cylindrical-shaped chip holding part 12 of the third exemplary embodiment is longer than chip holding part 12 of the first exemplary embodiment and furthermore sensor chip 4 is disposed at the top end thereof, and chip holding part 12 is inserted into opening 32 of socket 31 as shown in FIG. 9. Furthermore, electrode 9 at the lower part is inserted into opening 32 of socket 31.

That is to say, in the third exemplary embodiment, unlike the structure of the first exemplary embodiment in which the plurality of sensor chips 4 share one flow passage 7, each sensor chip 4 has one flow passage 7 as shown in FIG. 9.

The inside of chip holding part 12 has large capacity and functions as an electrolytic bath. An electrolytic solution can be filled in or sucked from the lower part of chip holding part 12.

In the third exemplary embodiment, since the inner wall of the electrolytic bath at the lower side is formed of hydrophilic chip holding part 12, foams generated inside the lower side electrolytic bath can be reduced.

Furthermore, when an electrolytic solution is sucked from the lower part of sensor chip 4 to an electrolytic bath at the upper side of the sensor chip, pressure tends to be applied, thus facilitating trapping of a cell to the opening of continuity hole 14. As a result, the measurement accuracy of the cell electrophysiological sensor can be improved.

Furthermore, in the third exemplary embodiment, since socket 31 is made of resin, it can be processed into a desired shape. For example, it is extended to the lower part than chip holding part 12, thereby the inside of socket 31 also functions as the lower side electrolytic bath. Then, the volume of the electrolytic bath at the lower part of sensor chip 4 can be freely changed by extending the length of socket 31, so that an excellent repairability is achieved.

Note here that in the third exemplary embodiment, sensor chip 4 is inserted into the upper end of cylindrical-shaped chip holding part 12. However, as in the first exemplary embodiment, it may be inserted into the lower end of chip holding part 12. In this case, since the inside of chip holding part 12 and the inside of opening 32 of socket 31 function as an electrolytic bath, well plate 1 is not needed.

Also in this case, the occurrence of foams can be suppressed and an excellent repairability is achieved.

(Fourth Exemplary Embodiment)

Figure 10:
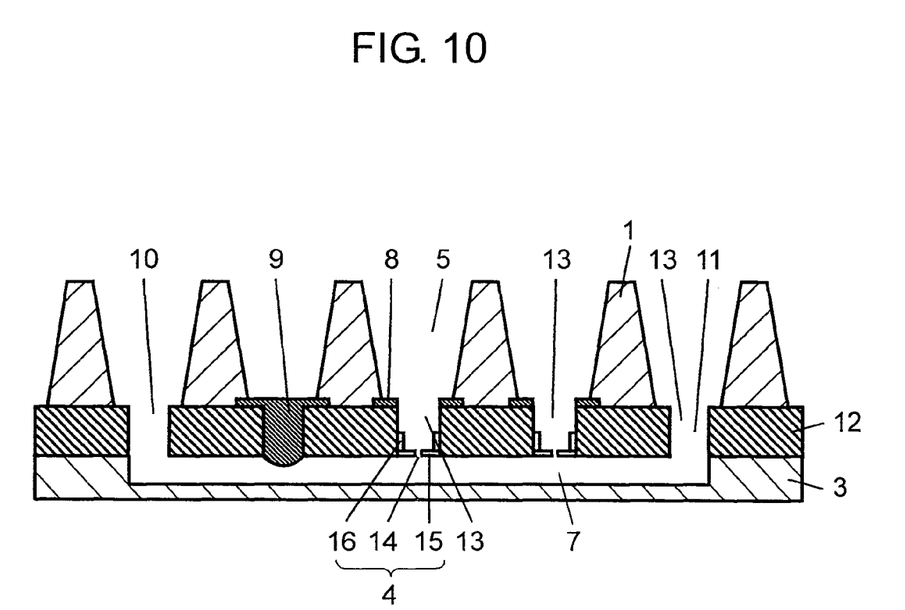
FIG. 10 is a sectional view showing a cell electrophysiological sensor in accordance with a fourth exemplary embodiment of the present invention.

FIG. 10 is a sectional view showing a cell electrophysiological sensor in accordance with a fourth exemplary embodiment of the present invention. The same reference numerals are given to the same configurations as in the first to third second exemplary embodiments and the description thereof is omitted herein.

The fourth exemplary embodiment is different from the first exemplary embodiment in that chip holding part 12 is formed in a plate shape as shown in FIG. 10. That is to say, chip holding part 12 of the fourth exemplary embodiment is a glass plate and this glass plate is provided with a plurality of through holes 13.

Then, sensor chip 4 made of silicon is inserted into the inside of through hole 13.

For example, in the fourth exemplary embodiment, as chip holding part 12, a 0.75 mm-thick glass plate of borosilicate glass is provided with through holes 13 by etching process.

The internal wall of through hole 13 may further be treated to have hydrophilic property or a hydrophilic film may be formed.

Then, after chip holding part 12 is held horizontally, sensor chip 4 stored in pure water is taken out and a part of the sensor chip 4 is inserted into the inlet port of through hole 13 from the upper surface of chip holding part 12 in a state in which pure water is attached to sensor chip 4. The inserted sensor chip 4 is self-aligned in a predetermined position due to the interaction of surface tension of pure water.

Then, as in the first exemplary embodiment, drying treatment and joining treatment may be carried out at one time.

At this time, it is confirmed that the side surface of sensor chip 4 and the through hole can be joined by glass welding when the gap between them is not more than 50 μm. The glass welding can be carried out efficiently when, for example, the outer diameter (dimension) of sensor chip 4 is made to be 700 μm, the inner diameter (dimension) of through hole 13 is made to be 750 μm. At that time, the joining by glass welding can be carried out under the heat treatment condition in which a welding temperature is 718° C. and a welding time is not more than 10 seconds.

Also in the fourth exemplary embodiment, since sensor chip 4 including silicon and chip holding part 12 including glass are adhesively bonded to each other by glass welding, chip holding part 12 can be strongly joined to substantially entire side surface of sensor chip 4. Therefore, the airtightness between the side surface of sensor chip 4 and chip holding part 12 is increased. As a result, a leakage current can be reduced.

Furthermore, as in the first exemplary embodiment, when sensor chip 4 is inserted into through hole 13 of chip holding part 12, by treating sensor chip 4 is treated to have hydrophilic property, the self-alignment property is improved.

In addition, as compared with the case where the silicon substrate and sensor chip 4 are integrated with each other, in the fourth exemplary embodiment, chip holding part 12 having large capacity can be formed of a relatively cheap glass plate, thus reducing the cost. Furthermore, when a part of sensor chip 4 is defective, it can be repaired so that the yield is improved.

(Industrial Applicability)

As mentioned above, since a cell electrophysiological sensor in accordance with the present invention enables efficient measurement of a plurality of cells at one time with a high accuracy, it is useful for measurement of the electrophysiological phenomenon of cells.

The invention claimed is:

1. A cell electrophysiological sensor device, comprising:
   a sensor chip having a side surface around said sensor chip and a bottom surface at a bottom of said sensor chip, said bottom surface having a continuity hole therein;
   a chip holding part around the side surface of the sensor chip; and
   an outside of the side surface of the sensor chip has an alternating convex and concave shape extending from a bottom portion to a top portion of the sensor chip, wherein the chip holding part is adhesively bonded to the side surface of the sensor chip.

2. The cell electrophysiological sensor device of claim 1, wherein the bottom surface of the sensor chip includes a thin plate having the continuity hole, and a frame body formed on one surface of the thin plate.

3. The cell electrophysiological sensor device of claim 1, wherein the bottom surface of the sensor chip includes a disk-shaped thin plate having the continuity hole, and a cylindrical-shaped frame body formed on one surface of the thin plate.

4. The cell electrophysiological sensor device of claim 1, wherein the chip holding part has a cylindrical shape or a plate shape having a through hole.

5. The cell electrophysiological sensor device of claim 1, wherein the chip holding part has a cylindrical shape and is inserted into a through hole of a plate-shaped holding plate.

6. The cell electrophysiological sensor device of claim 1, wherein an inner wall of the chip holding part has a curved surface communicating with at least one of an upper surface and a lower surface of the sensor chip.

7. The cell electrophysiological sensor device of claim 1, wherein the chip holding part is made of glass having a glass softening point of not lower than 500° C. and not higher than 900° C.

8. The cell electrophysiological sensor device of claim 1, wherein the chip holding part is made of glass having a contact angle with respect to water of more than 0° and not more than 10°.

9. The cell electrophysiological sensor device of claim 1, wherein the chip holding part is made of glass containing silicon dioxide.

10. The cell electrophysiological sensor device of claim 1, wherein the chip holding part is made of glass having ultraviolet ray transmittance of not less than 70% and less than 100% in a wavelength range from 380 nm to 340 nm.

11. The cell electrophysiological sensor device of claim 1, wherein the outside of the side surface is a laminate.

12. The cell electrophysiological sensor device of claim 1, wherein the side surface of the sensor chip is hydrophilic.

13. The cell electrophysiological sensor device of claim 1, wherein a hydrophilic film is formed on the side surface of the sensor chip.

14. The cell electrophysiological sensor device of claim 1, wherein a hydrophilic film including silicon oxide or silicon nitride is included in the side surface of the sensor chip.

15. The cell electrophysiological sensor device of claim 1, wherein an inner part of a side surface of the sensor chip has concave and convex parts.

16. A cell electrophysiological sensor device, comprising:
a sensor chip having a side surface around said sensor chip and a bottom surface at a bottom of said sensor chip, said bottom surface having a continuity hole therein;
a chip holding part around the side surface of the sensor chip; and
an outside of the side surface of the sensor chip has an alternating convex and concave shape extending from a bottom portion to a top portion of the sensor chip,
wherein the sensor chip includes silicon,
the chip holding part includes glass, and
the chip holding part is bonded to the side surface of the sensor chip.

* * * * *